United States Patent
Das et al.

(10) Patent No.: US 9,701,598 B2
(45) Date of Patent: Jul. 11, 2017

(54) PROCESS FOR REMOVING OXYGENATED CONTAMINATES FROM AN ETHYLENE STREAM

(75) Inventors: Babua Das, Evere (BE); Manuela Arratia, Paris (FR); Catherine Boutrot, Chatou (FR)

(73) Assignee: Total Research & Technology Feluy, Seneffe (BE)

(*) Notice: Subject to any disclaimer, the term of this patent is extended or adjusted under 35 U.S.C. 154(b) by 540 days.

(21) Appl. No.: 14/235,251

(22) PCT Filed: Jul. 13, 2012
(Under 37 CFR 1.47)

(86) PCT No.: PCT/EP2012/063754
§ 371 (c)(1),
(2), (4) Date: Apr. 10, 2014

(87) PCT Pub. No.: WO2013/014002
PCT Pub. Date: Jan. 31, 2013

(65) Prior Publication Data
US 2014/0303422 A1 Oct. 9, 2014

(30) Foreign Application Priority Data
Jul. 28, 2011 (EP) .................................. 11290350

(51) Int. Cl.
C07C 7/00 (2006.01)
C07C 7/12 (2006.01)

(52) U.S. Cl.
CPC ............... *C07C 7/005* (2013.01); *C07C 7/00* (2013.01); *C07C 7/12* (2013.01)

(58) Field of Classification Search
None
See application file for complete search history.

(56) References Cited

U.S. PATENT DOCUMENTS 6,444,869 B2   9/2002   Senetar et al.
7,223,895 B2   5/2007   Sumner
(Continued)

FOREIGN PATENT DOCUMENTS

WO   03/020670 A1   3/2003
WO   03/020672 A1   3/2003
(Continued)

OTHER PUBLICATIONS

International Search Report issued in PCT/EP2012/063754 mailed on Sep. 28, 2012 (3 pages).
(Continued)

*Primary Examiner* — Tam M Nguyen
(74) *Attorney, Agent, or Firm* — Albert Shung (57) ABSTRACT

The present invention is, in a first embodiment, a process for removing oxygenated contaminants from an ethylene stream comprising:
a) providing a dried ethylene stream (A) comprising essentially ethylene, up to 1 w % oxygenates, ethane, CO, $CO_2$, $H_2$, $CH_4$ and C3+ hydrocarbons,
b) sending said stream (A) to a stripper (also referred to as a demethanizer) to produce
an overhead stream comprising essentially CO, $H_2$ and $CH_4$,
a bottom stream comprising essentially ethylene, oxygenates, ethane, $CO_2$ and C3+ hydrocarbons,
c) sending said bottom stream of step b) to a deethanizer to produce
a bottom stream comprising essentially ethane, oxygenates and C3+ hydrocarbons,
an overhead stream consisting essentially of ethylene and $CO_2$,
d) sending said overhead of step c) to a fixed bed $CO_2$ adsorption zone to recover an ethylene stream essentially free of $CO_2$.

(Continued)

In another embodiment the CO2 adsorption zone can be located at the inlet of the deethanizer.

In another embodiment the demethanizer is replaced by two demethanizers.

In another embodiment the deethanizer is replaced by two C2 splitters.

12 Claims, 4 Drawing Sheets

(56) References Cited

U.S. PATENT DOCUMENTS

| | | | | |
|---|---|---|---|---|
| 9,328,297 B1* | 5/2016 | Nyce | ............... | C10G 50/00 |
| 2003/0098281 A1 | 5/2003 | Shutt et al. | | |
| 2005/0283038 A1 | 12/2005 | Kuechler et al. | | |
| 2014/0303422 A1* | 10/2014 | Das | ............... | C07C 7/005 |
| | | | | 585/809 |
| 2015/0330706 A1* | 11/2015 | Vermeiren | ............... | C07C 1/24 |
| | | | | 62/620 |

FOREIGN PATENT DOCUMENTS

| | | |
|---|---|---|
| WO | 03/033438 A1 | 4/2003 |
| WO | 2004/011404 A1 | 2/2004 |
| WO | 2008/042613 A2 | 4/2008 |
| WO | 2009/098262 A1 | 8/2009 |
| WO | 2009/098267 A1 | 8/2009 |
| WO | 2009/098268 A1 | 8/2009 |
| WO | 2009/098269 A1 | 8/2009 |
| WO | 2011/076752 A1 | 6/2011 |

OTHER PUBLICATIONS

Colombian Office Action issued in Application No. 14-034851, dated Jul. 21, 2015, 28 pages.

* cited by examiner

PROCESS FOR REMOVING OXYGENATED CONTAMINATES FROM AN ETHYLENE STREAM

CROSS-REFERENCE TO RELATED APPLICATIONS

This application claims the benefit of PCT/EP2012/063754, filed on Jul. 13, 2012, which claims priority from EP 11290350.5, filed on Jul. 28, 2011.

FIELD OF THE INVENTION

The present invention is a process for removing oxygenated contaminants from an ethylene stream.

Olefins are traditionally produced from petroleum feedstocks by catalytic or steam cracking processes. These cracking processes, especially steam cracking, produce light olefin(s), such as ethylene and/or propylene, from a variety of hydrocarbon feedstock. Ethylene and propylene are important commodity petrochemicals useful in a variety of processes for making plastics and other chemical compounds. The limited supply and increasing cost of crude oil has prompted the search for alternative processes for producing hydrocarbon products.

Olefins can be produced by dehydration of the corresponding alcohol. Ethanol can be obtained by fermentation of carbohydrates. Made up of organic matter from living organisms, biomass is the world's leading renewable energy source. The effluent produced by the ethanol dehydration comprises essentially unconverted ethanol, water, ethylene, acetaldehyde. Acetaldehyde may cause problems in ethylene recovery operations. It may comprise also very small amounts of ethane, CO, CO2, H2, CH4 and C3+ hydrocarbons. The weight ratio of ethane+CO+CO2+H2+CH4+C3+ hydrocarbons to ethylene is most of time less than 20/80.

BACKGROUND OF THE INVENTION

US 20030098281 A1 describes a method of controlling water and/or oxygenate concentrations of an olefin stream. The method includes contacting the olefin stream with a liquid absorbent. The liquid absorbent is selected from the group consisting of a polyol, amine, amide, nitrile, heterocyclic nitrogen containing compound, and mixtures thereof. A gaseous stream comprising essentially steam, ethylene, propylene and less than 2 w % of oxygenates is condensed in a quench tower. The overhead of said quench tower is washed with a caustic solution to remove CO2 and then contacted with the liquid absorbent to remove the oxygenates.

WO 03 020670 A1 provides a method for removing oxygenated components such as acetaldehyde, CO2 and/or water from an olefin stream. It explains it is desirable to remove such oxygenated components, since they may poison catalysts that are used to further process olefin composition. In addition, the presence of certain oxygenated compounds, such as acetaldehyde, can cause fouling in other olefin purification units, e.g., acid gas treating units. The method comprises providing an olefin stream containing ethylene, propylene, C4+ olefins and acetaldehyde. The olefin stream is separated into a first fraction and a second fraction, wherein the first fraction comprises at least a majority of the ethylene and/or propylene present in the olefin stream, and the second fraction comprises at least a majority of the C4+ olefins and acetaldehyde present in the olefin stream. The first fraction is then acid gas treated by sodium hydroxide or potassium hydroxide. The olefin stream is separated by distillation, preferably, the distillation is extractive distillation using an extractant. The preferred extractant is a polar composition having an average boiling point of at least 38° C. at 1 atm. Methanol is one type of preferred extractant.

WO 03 020672 A1 describes method of removing dimethyl ether from an ethylene and/or propylene containing stream. The olefin stream is passed to a water absorption column, methanol is used as the water absorbent. Methanol and entrained water, as well as some oxygenated hydrocarbon, is recovered as the bottoms stream of said water absorption column, an overhead olefin is recovered and sent to a distillation column. The distillation column separates ethylene and propylene, as well as lighter boiling point components from the dimethyl ether and heavier boiling point components, including C4+ components and methanol remaining from the methanol wash. Additional methanol is added to the distillation column to reduce clathrate and/or free water formation in the distillation column. The ethylene and propylene containing stream exits the distillation column as overhead and the heavier boiling point components which include the dimethyl ether and C4+ components exit the distillation column as the bottoms. Ethylene and propylene then flow to a caustic wash column.

WO 03 033438 A1 describes a method for processing an olefin stream containing oxygenates and water, comprising: providing an olefin stream containing oxygenates and water; dewatering the olefin stream; compressing the dewatered olefin stream; washing the olefin stream with methanol to remove at least a portion of the oxygenate from the olefin stream; contacting the methanol washed olefin stream with water; and fractionating the water contacted olefin stream. The revovered olefin stream (washed with methanol and then with water) is further sent to an alkali wash and a drying step. The olefin stream containing oxygenates and water is the effluent of an MTO process.

U.S. Pat. No. 6,444,869 describes a process for the production of ethylene from an oxygenate conversion effluent stream. The oxygenate conversion effluent stream comprises hydrogen, methane, ethylene, ethane, propylene, propane and C4+ olefins. This effluent is compressed, treated to remove oxygenates, passed to a carbon dioxide removal zone wherein carbon dioxide is absorbed by contacting a caustic solution or by contacting an amine solution in combination with a caustic solution in a conventional manner to remove the carbon dioxide, dried, then fractionation is made through a deethanizer and a demethanizer.

US 2005-0283038 A1 described a process for producing an olefins stream from a first vapor effluent stream from an oxygenate to olefin conversion reaction, said first vapor effluent stream comprising C2 and C3 olefins, C4 hydrocarbons, and C2 to C6 carbonyl compounds. In the process, the temperature and pressure of the first vapor effluent stream are adjusted to produce a second vapor effluent stream having a pressure ranging from about 100 psig to about 350 psig (790 to 2514 kPa) and a temperature ranging from about 70° F. to about 120° F. (21 to 49° C.), said second vapor effluent stream containing about 50 wt. % or more C4 hydrocarbons based upon the total weight of C4 hydrocarbons in the first vapor effluent stream. The second vapor effluent stream is then washed with a liquid alcohol-containing stream to produce a third vapor effluent stream, whereafter the third vapor effluent stream is washed with liquid water to provide a fourth vapor effluent stream comprising the C2 and C3 olefins and about 1.0 wt. % or less C2 to C6 carbonyl compounds. In one embodiment of such a recovery process, at least part of the fourth vapor effluent stream is contacted with a basic component, such as caustic or an amine, to remove the bulk of the carbon dioxide therefrom (thus removing "acid gas" from the fourth vapor effluent stream), whereafter the $CO_2$-depleted stream is dried.

The main drawback of the above prior arts is the fouling of the caustic scrubber. The inlet gas to the caustic scrubber contains reactive oxygenates like aldehydes and ketones. These aldehydes react in the aldol condensation reaction in the caustic tower environment to form significant red oil polymers. This causes significant fouling concerns in the caustic tower which impact the unit run length. The spent caustic treatment with significant red oil polymer content is also an important concern as well as the spent caustic treatment and disposal issues. In addition there are the handling and disposal issues of red oil polymers.

It has now been discovered a process for removing oxygenated contaminants from an ethylene stream wherein there is no caustic wash to remove the CO2 and no wash column to remove the oxygenates.

BRIEF SUMMARY OF THE INVENTION

The present invention is, in a first embodiment, a process for removing oxygenated contaminants from an ethylene stream comprising:
a) providing a dried ethylene stream (A) comprising essentially ethylene, up to 1 w % oxygenates, ethane, CO, CO2, H2, CH4 and C3+ hydrocarbons,
b) sending said stream (A) to a stripper (also referred to as a demethanizer) to produce an overhead stream comprising essentially CO, H2 and CH4, a bottom stream comprising essentially ethylene, oxygenates, ethane, $CO_2$ and C3+ hydrocarbons, and
(i)
c) sending said bottom stream of step b) to a deethanizer to produce a bottom stream comprising essentially ethane, oxygenates and C3+ hydrocarbons,
an overhead stream consisting essentially of ethylene and CO2,
d) sending said overhead of step c) to a fixed bed CO2 adsorption zone to recover an ethylene stream essentially free of CO2,
or (ii)
c1) sending said bottom stream of step b) to a fixed bed CO2 adsorption zone to recover a stream essentially free of CO2, then sending said stream to a deethanizer to produce
a bottom stream comprising essentially ethane, oxygenates and C3+ hydrocarbons,
an overhead stream consisting essentially of ethylene essentially free of CO2.
The above process is referred to as embodiment 1.
In a second embodiment the deethanizer of embodiment 1 is replaced by two C2 splitters.

Said second embodiment is a process for removing oxygenated contaminants from an ethylene stream comprising:
a) providing a dried ethylene stream (A) comprising essentially ethylene, up to 1 w % oxygenates, ethane, CO, CO2, H2, CH4 and C3+ hydrocarbons,
b) sending said stream (A) to a stripper (also referred to as a demethanizer) to produce
an overhead stream comprising essentially CO, H2 and CH4,
a bottom stream comprising essentially ethylene, oxygenates, ethane, CO2 and C3+ hydrocarbons, and
(i)
c) sending said bottom stream of step b) to a primary C2 splitter to produce a bottom stream comprising essentially ethane, oxygenates, C3+ hydrocarbons and a portion of ethylene,
an overhead stream consisting essentially of ethylene and CO2,
d) sending said overhead of step c) to a fixed bed CO2 adsorption zone to recover an ethylene stream essentially free of CO2,
e) sending the bottom stream of step c) to a secondary C2 splitter to produce a bottom stream comprising essentially ethane, oxygenates and C3+ hydrocarbons,
an overhead stream consisting essentially of ethylene, optionally recycled to the production zone of stream (A),
Or (ii)
c1) sending said bottom stream of step b) to a fixed bed CO2 adsorption zone to recover a stream essentially free of CO2, then sending said stream to a primary C2 splitter to produce a bottom stream comprising essentially ethane, oxygenates, C3+ hydrocarbons and a portion of ethylene,
an overhead stream consisting essentially of ethylene essentially free of CO2,
e1) sending the bottom stream of step c1) to a secondary C2 splitter to produce
a bottom stream comprising essentially ethane, oxygenates and C3+ hydrocarbons,
an overhead stream consisting essentially of ethylene, optionally recycled to the production zone of stream (A).
In a third embodiment the demethanizer (stripper) of embodiment 1 is replaced by two demethanizers.

Said third embodiment is a process for removing oxygenated contaminants from an ethylene stream comprising:
a) providing a dried ethylene stream (A) comprising essentially ethylene, up to 1 w % oxygenates, ethane, CO, CO2, H2, CH4 and C3+ hydrocarbons,
b) sending said stream (A) to a primary demethanizer to produce
an overhead stream comprising essentially CO, H2, CH4 and a portion of ethylene and ethane,
a bottom stream comprising essentially ethylene, oxygenates, ethane, CO2 and C3+ hydrocarbons,
c) sending said overhead stream of step b), optionally through a compressor, to a secondary demethanizer to produce
an overhead stream comprising essentially CO, H2 and CH4,
a bottom stream comprising essentially ethylene, oxygenates, ethane, CO2 and C3+ hydrocarbons, and
(i)
d) sending said bottom stream of step b) and said bottom stream of step c) to a C2 splitter to produce
a bottom stream comprising essentially ethane, oxygenates and C3+ hydrocarbons,
an overhead stream consisting essentially of ethylene and CO2,
e) sending said overhead of step d) to a fixed bed CO2 adsorption zone to recover an ethylene stream essentially free of CO2,
or (ii)
d1) sending said bottom stream of step b) and said bottom stream of step c) to a fixed bed CO2 adsorption zone to recover a stream essentially free of CO2, then sending said stream to a C2 splitter to produce
a bottom stream comprising essentially ethane, oxygenates and C3+ hydrocarbons,
an overhead stream consisting essentially of ethylene essentially free of CO2.

In an embodiment the weight ratio of ethane+CO+CO2+ H2+CH4+C3+ hydrocarbons to ethylene in (A) is less than 10/90.

In an embodiment the weight ratio of ethane+CO+CO2+ H2+CH4+C3+ hydrocarbons to ethylene in (A) is less than 10/90 and above 0.1/99.9.

In an embodiment the weight ratio of ethane+CO+CO2+ H2+CH4+C3+ hydrocarbons to ethylene in (A) is less than 5/95.

In an embodiment the proportion of oxygenates in (A) is from 50 wppm to 7000 wppm.

In an embodiment the proportion of oxygenates in (A) is up to 3000 wppm.

In an embodiment the proportion of oxygenates in (A) is up to 2000 wppm.

In an embodiment the proportion of H2 in (A) is from 5 to 1000 wppm.

In an embodiment the proportion of H2 in (A) is up to 800 wppm.

In an embodiment the proportion of H2 in (A) is up to 500 wppm.

Advantageously "dried ethylene stream" at step a) means a water content less than 5 wppm, advantageously less than 3 wppm and preferably less than 1 wppm.

In an embodiment when the dried ethylene stream (A) has been made by ethanol dehydration said stream (A) contains substantially no acetylene.

Ethylene treated in accordance with this invention is particularly suitable for use as feedstock for making alpha-olefins, ethylbenzene/styrene, ethyleneoxide/ethyleneglycol, ethylenedichloride and corresponding polymers, like polyethylene homo or copolymer (PE, EPR, EPDM etc), polystyrene (PS), styrene copolymers with butadiene, isoprene, acrylonitrile or combinations (SBS, SIS, SBR, ABS, SAN), polyesters (PET) and polyvinylchlorides (PVC).

DETAILED DESCRIPTION OF THE INVENTION

As regards the oxygenated contaminants also referred to as oxygenates, one can cite ethanol, C3 alcohols; ethers such as diethylether and methyl ethyl ether; carboxylic acids such as acetic acid; aldehydes such as acetaldehyde; ketones such as acetone; and esters such as methyl esters. Particularly problematic oxygenate contaminants in an alcohol dehydration are aldehydes.

As regards the ethylene stream (A) of step a), it can be originating from the dehydration of ethanol. Said dehydration can be made in one or more ethanol dehydration reactors. As regards alcohol dehydration, such process is described in WO-2009-098262, WO-2009-098267, WO-2009-098268 and WO-2009-098269 the content of which is incorporated in the present application. The present invention is very efficient for the purification of ethylene produced by dehydration of ethanol.

The outlet of said dehydration reactor comprises essentially ethylene and steam as well as minor amounts of oxygenates, ethane, CO, CO2, H2, CH4 and C3+ hydrocarbons. "Minor amounts" means the weight ratio of ethane+ CO+CO2+H2+CH4+C3+ hydrocarbons to ethylene is less than 20/80 and most of time less than 10/90.

Said outlet of dehydration reactor is initially cooled, typically in a quench tower employing water as the quench medium. In the quench tower, most of the water contained in the outlet of dehydration reactor is condensed and is removed from the bottom of the tower as a liquid water bottom stream. A part of said water bottom stream is cooled in a heat exchanger and recycled as quenching medium to the top of the quench column. The part of the water bottom stream which is not recycled as quenching medium may contain a part of the oxygenates and mostly unconverted ethanol if any. Said stream can be treated in a stripping column to recover a pure water stream. Ethylene, oxygenates, ethane, CO, CO2, H2, CH4 and C3+ hydrocarbons are removed from the top of the quench tower at a pressure typically such as 1 to 16 bars absolute and are referred to as the contaminated ethylene stream. Advantageously said contaminated ethylene stream is successively compressed and cooled in one or more steps to remove the major part of water, further fed to a fixed bed drying zone and finally to the process of the invention.

In the previous compression steps the recovered water contains a part of the oxygenated contaminants and hydrocarbons dissolved. The contaminated hydrocarbon stream can also be cooled before the first compression step and water recovered. In an embodiment the water recovered upon each cooling further to a compression step and upon cooling, if any, before the first compression step is sent to a stripping column to produce an overhead stream comprising essentially oxygenated contaminants and hydrocarbons and an essentially pure water bottoms stream. Optionally the overhead stream is burned to destroy the oxygenated contaminants and recover heat.

After the compression steps the contaminated ethylene stream is further fed to a fixed bed drying zone and finally to the process of the present invention. The fixed bed drying zone is known in itself.

As regards the fixed bed CO2 adsorption zone, it can be any component capable to selectively remove CO2. By way of example it is an available commercial fixed bed adsorption (PSA for pressure swing adsorption or TSA for temperature swing adsorption) using molecular sieves or basic oxides, supported basic oxides, high surface area carbons, organo-metallic framework components (MOF's) or mixture thereof. The molecular sieves are preferably low silica zeolites, having 8 (among which zeolite A) or 12 membered (among which zeolite X) rings and exchanged with alkali, alkaline earth or lanthanide cations. Other molecular sieves are crystalline titanosilicates (ETS family materials). Supported basic oxides are preferably, alkali, alkaline earth or lanthanide oxides supported on high surface area carbons, alumina, silica, zirconia or titania. The removal of CO2 can be carried out with a liquid stream or with a gaseous ethylene stream depending on the pressure and temperature. A stream essentially free of CO2 is recovered. As only trace amounts of CO2 have to be removed from the ethylene, the preferred process cycle is of the thermal swing adsorption (TSA) type. Said fixed bed adsorbent, once saturated with CO2, can be regenerated, during regeneration the desorption produces a stream which can be treated anywhere. In a TSA process cycle, the regeneration is done while sweeping the saturated adsorbent with an inert gas by increasing the temperature until desorption of the $CO_2$ occurs. Eventually the saturated adsorbent can be replaced by new adsorbent and the saturated adsorbent either be disposed of or regenerated ex-situ for further use. "Essentially" has to be interpretated in the light of the further use of ethylene. Should ethylene is to be polymerized $CO_2$ has to be 1 ppm vol or less and preferably 0.5 ppm vol or less.

As regards the demethanizer, it is also referred to as a stripper in first and second embodiments and as a primary and secondary demethanizer in the third embodiment. The purpose of said demethanizer is to recover an overhead comprising essentially $H_2$, $CH_4$ and CO. It is advantageously a distillation column.

As regards the operating conditions, the demethanizer has to be at a pressure high enough to operate at temperatures which are not too low. A demethanizer to recover an overhead comprising $H_2$, $CH_4$ and CO and essentially liquid ethylene at the bottoms operating at 40 barg has an overhead temperature of around 0 to $-10°$ C. and a bottom temperature of around $0°$ C. The same demethanizer operating at 21 barg has an overhead temperature of $-30°$ C. and a bottom temperature of around $-24°$ C. These temperatures and pressures are a function of the proportion of $H_2$, $CH_4$ and CO in the ethylene stream (A) and mainly of the proportion of $H_2$.

In an embodiment the pressure of the C2 splitter also referred to as a deethanizer is selected to have a temperature of the C2 splitter/deethanizer bottoms such as there is no oligomerization or polymerization of the oxygenates. By way of example said temperature should not exceed $150°$ C. and advantageously not exceed $100°$ C. This temperature is function of the pressure and of the proportion of oxygenates in the mixture of oxygenates+ethane+C3+ hydrocarbons. The higher the proportion of oxygenates the higher the temperature. The higher the pressure the higher the temperature. The C2 splitter/deethanizer is advantageously a distillation column.

As regards the first embodiment and the stripper, it is advantageously a distillation column. The overhead is a mixture of essentially CO, $H_2$ and $CH_4$. The deethanizer is advantageously a distillation column. The fixed bed $CO_2$ adsorption zone can be an available commercial fixed bed adsorption (TSA or PSA) as described above. A stream essentially free of $CO_2$ is recovered.

In an embodiment the stripper (demethanizer) and the C2 splitter/deethanizer are operating at the same pressure except the pressure drop between the demethanizer and the C2 splitter/deethanizer for transfer of fluids. Advantageously the pressure is ranging from 15 to 45 barg.

Figure 1:
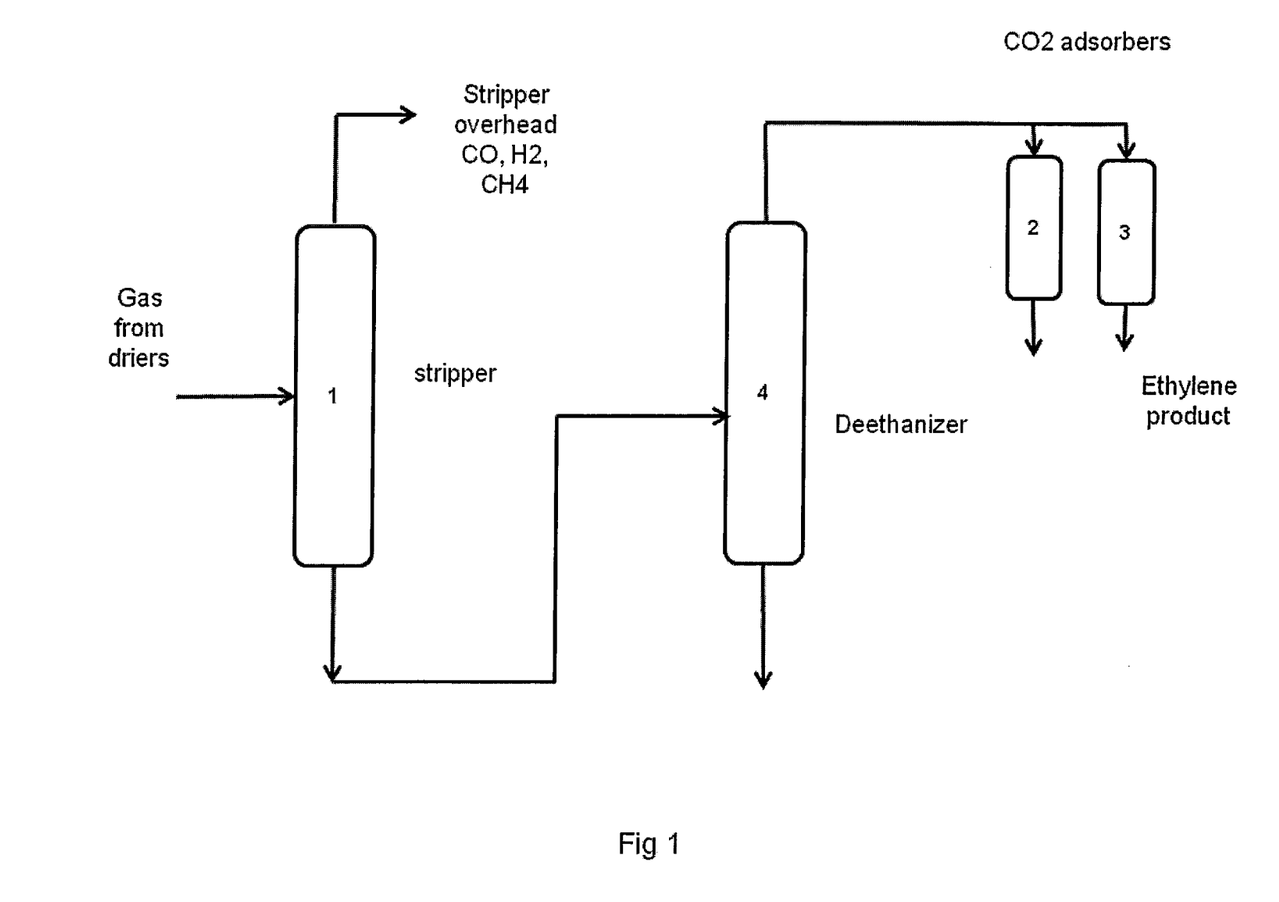
FIG. 1 depicts a process according to the first embodiment with the stripper (demethanizer), the $CO_2$ adsorbers, and the deethanizer.

A process according to the first embodiment is described on FIG. 1 wherein 1 is the stripper (demethanizer), 2 and 3 the $CO_2$ adsorbers and 4 the deethanizer. On top of the stripper there are a condenser, a decanter producing a liquid phase sent as a reflux to said stripper and a gaseous phase which is the overhead, they are not shown on the FIG. 1. On the bottom of the stripper there is a reboiler not shown on FIG. 1. The deethanizer has a similar equipment not shown on FIG. 1. The contaminated ethylene stream (A) comprising essentially ethylene, up to 1 w % oxygenates, ethane, CO, $CO_2$, $H_2$, $CH_4$ and C3+ hydrocarbons has been dried and sent to the stripper 1 (also referred to as a demethanizer) to produce an overhead stream comprising essentially CO, $H_2$ and $CH_4$, a bottom stream comprising essentially ethylene, oxygenates, ethane, $CO_2$ and C3+ hydrocarbons, said bottom stream of the stripper 1 is sent to the deethanizer 4 to produce a bottom stream comprising essentially ethane, oxygenates and C3+ hydrocarbons, an overhead stream consisting essentially of ethylene and $CO_2$, said overhead of deethanizer 4 is sent to a fixed bed $CO_2$ adsorption zone 2 and 3 to recover an ethylene stream essentially free of $CO_2$.

In a specific example the pressure of the stripper ranges from 15 to 30 barg and the pressure of the deethanizer and the $CO_2$ adsorbers is about 1 or 2 barg less corresponding to the pressure drop due to pipes and equipment. In this range of pressure the temperature on top of stripper and after the condenser ranges from $-20$ to $-30°$ C., the temperature on bottom of stripper ranges from $-15$ to $-25°$ C., the temperature on top of deethanizer and after the condenser ranges from $-30$ to $-20°$ C. and the temperature on bottom of deethanizer ranges from 75 to $85°$ C.

Preferably the pressure of the stripper ranges from 20 to 25 barg and the pressure of the deethanizer and the $CO_2$ adsorbers is about 1 or 2 barg less corresponding to the pressure drop due to pipes and equipment. In this range of pressure the temperature on top of stripper and after the condenser ranges from $-22$ to $-26°$ C., the temperature on bottom of stripper ranges from $-20$ to $-24°$ C., the temperature on top of deethanizer and after the condenser ranges from $-27$ to $-22°$ C. and the temperature on bottom of deethanizer ranges from 78 to $82°$ C.

In another specific example the pressure of the stripper ranges from 35 to 45 barg and the pressure of the deethanizer and the $CO_2$ adsorbers is about 15 to 25 barg less. Advantageously the pressure of the deethanizer ranges from 15 to 25 barg. In this range of pressure the top of stripper is at a temperature in the range $-10$ to $0°$ C. and condensed at a temperature ranging from $-35$ to $-45°$ C., the temperature on bottom of stripper ranges from $-5$ to $5°$ C., the temperature on top of deethanizer ranges from $-25$ to $-35°$ C., is condensed at a temperature in the range $-25$ to $-35°$ C. and the temperature on bottom of deethanizer ranges from 75 to $85°$ C.

Preferably the pressure of the stripper ranges from 38 to 42 barg and the pressure of the deethanizer and the $CO_2$ adsorbers ranges from 17 to 22 barg. In this range of pressure the top of stripper is at a temperature in the range $-8$ to $-2°$ C. and condensed at a temperature ranging from $-38$ to $-42°$ C., the temperature on bottom of stripper ranges from 0 to $5°$ C., the temperature on top of deethanizer ranges from $-28$ to $-32°$ C., is condensed at a temperature in the range $-28$ to $-32°$ C. and the temperature on bottom of deethanizer ranges from 78 to $82°$ C.

As regards the second embodiment and the demethanizer, it is advantageously a distillation column. The primary and secondary splitters are each advantageously a distillation column. The fixed bed $CO_2$ adsorption zone has already been described above. A stream essentially free of $CO_2$ is recovered.

In an embodiment the demethanizer and the primary and secondary C2 splitter/deethanizer are operating at the same pressure except the pressure drop for transfer of fluids. Advantageously the pressure is ranging from 15 to 45 barg.

Figure 2:
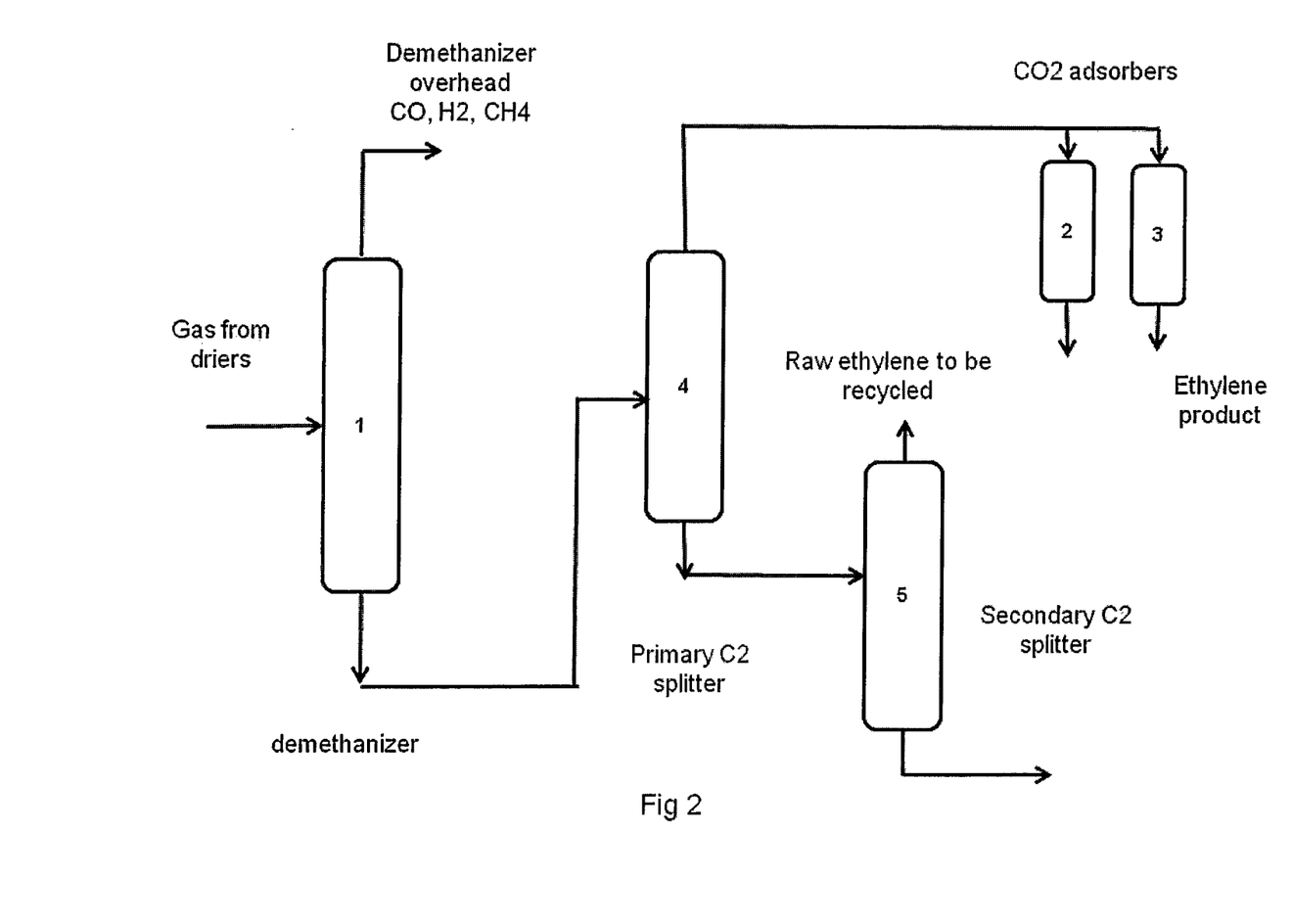
FIG. 2 depicts a process according to the second embodiment with the demethanizer, the $CO_2$ adsorbers, the primary $C_2$ splitter, and the secondary $C_2$ splitter.

A process according to the second embodiment is described on FIG. 2 wherein 1 is the demethanizer, 2 and 3 the $CO_2$ adsorbers, 4 the primary C2 splitter and 5 the secondary C2 splitter. On top of the demethanizer there are a condenser, a decanter producing a liquid phase sent as a reflux to said demethanizer and a gaseous phase which is the overhead, they are not shown on the FIG. 2. On the bottom of the demethanizer there is a reboiler not shown on FIG. 2. The primary C2 splitter and the secondary C2 splitter have each a similar equipment not shown on FIG. 2.

The contaminated ethylene stream (A) comprising essentially ethylene, up to 1 w % oxygenates, ethane, CO, CO2, H2, CH4 and C3+ hydrocarbons has been dried and sent to the demethanizer 1
to produce
an overhead stream comprising essentially CO, H2 and $CH_4$,
a bottom stream comprising essentially ethylene, oxygenates, ethane, CO2 and C3+ hydrocarbons,
said bottom stream of demethanizer 1 are sent to the primary C2 splitter 4 to produce
a bottom stream comprising essentially ethane, oxygenates, C3+ hydrocarbons and a portion of ethylene,
an overhead stream consisting essentially of ethylene and CO2,
said overhead of the primary C2 splitter 4 is sent to a fixed bed CO2 adsorption zone 2 and 3 to recover an ethylene stream essentially free of CO2,
the bottom stream of the primary C2 splitter 4 is sent to a secondary C2 splitter 5 to produce
a bottom stream comprising essentially ethane, oxygenates and C3+ hydrocarbons,
an overhead stream consisting essentially of ethylene, optionally recycled to the production zone of stream (A).

In a specific example the pressure of the demethanizer ranges from 35 to 45 barg and the pressure of the primary C2 splitter and the CO2 adsorbers is about 1 or 2 barg less corresponding to the pressure drop due to pipes and equipment. The pressure of the secondary C2 splitter ranges from to 15 to 25 barg. In these ranges of pressure the top of demethanizer is at a temperature in the range −10 to 0° C., is condensed at a temperature ranging from −35 to −45° C., the temperature on bottom of demethanizer ranges from −5 to 5° C., the top of the primary C2 splitter is in a temperature range from −5 to 5° C., is condensed in a temperature range from −5 to 5° C., the temperature on bottom of primary C2 splitter ranges from 75 to 85° C., the top of the secondary C2 splitter is in a temperature range from −25 to −35° C., is condensed in a temperature range from −25 to −35° C. and the temperature on bottom of secondary C2 splitter ranges from 75 to 85° C.

Preferably the pressure of the demethanizer ranges from 38 to 42 barg and the pressure of the primary C2 splitter and the CO2 adsorbers is about 1 or 2 barg less corresponding to the pressure drop due to pipes and equipment. The pressure of the secondary C2 splitter ranges from to 18 to 22 barg. In these ranges of pressure the top of demethanizer is in a temperature range of −8° C. to −2° C., is condensed at a temperature ranging from −38 to −42° C., the temperature on bottom of demethanizer ranges from 0 to 4° C., the top of primary C2 splitter is in a temperature range from −4 to 0° C., is condensed in a temperature range from −4 to 0° C., the temperature on bottom of primary C2 splitter ranges from 78 to 82° C., the top of the secondary C2 splitter is in a temperature range from −28 to −32° C., is condensed in a temperature range from −28 to −32° C., and the temperature on bottom of secondary C2 splitter ranges from 78 to 82° C.

As regards the third embodiment and the primary and secondary demethanizer, they are each advantageously a distillation column. The C2 splitter is advantageously a distillation column. The fixed bed CO2 adsorption zone has already been described above. A stream essentially free of CO2 is recovered.

In an embodiment the primary, the secondary demethanizers and the C2 splitter/deethanizer are operating at the same pressure except the pressure drop for transfer of fluids. Advantageously the pressure is ranging from 15 to 45 barg.

Figure 3:
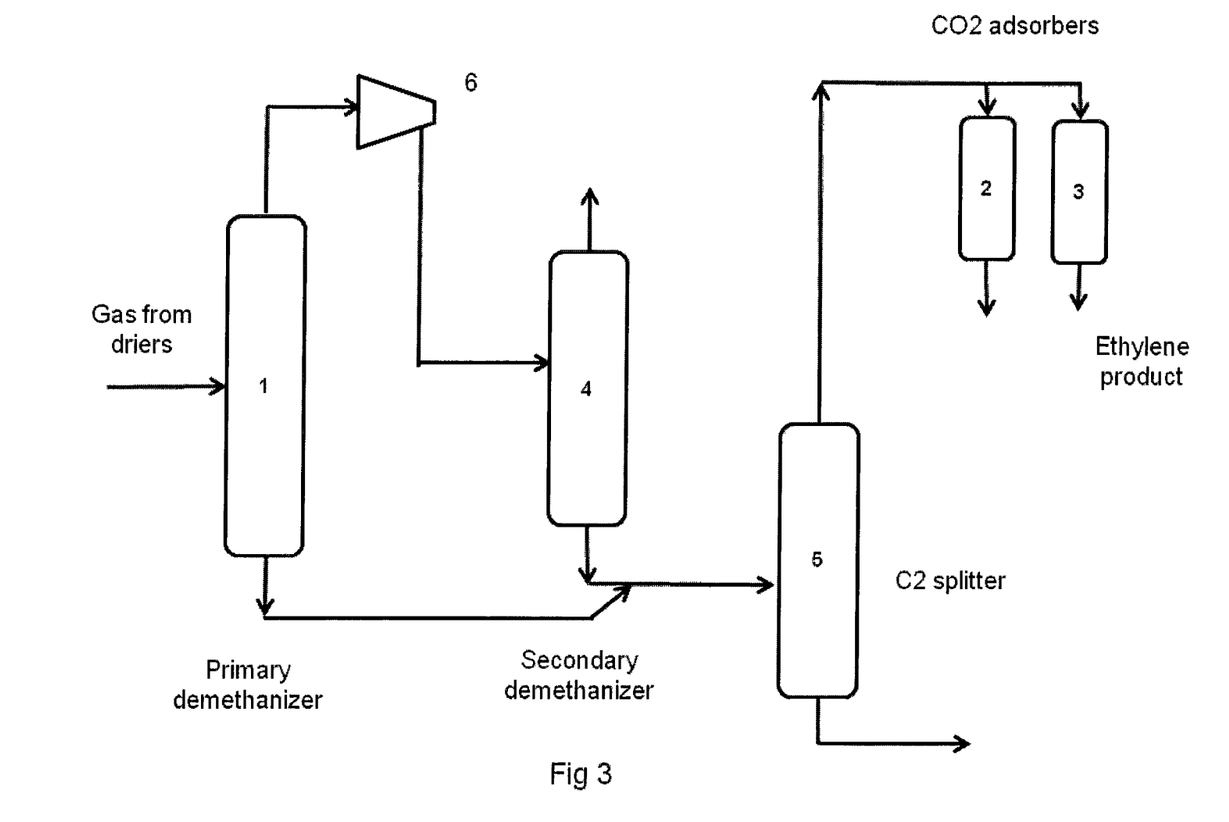
FIG. 3 depicts a process according to the third embodiment with the primary demethanizer, the $CO_2$ adsorbers, the secondary demethanizer, the $C_2$ splitter, and the compressor.

A process according to the third embodiment is described on FIG. 3 wherein 1 is the primary demethanizer, 2 and 3 the CO2 adsorbers, 4 the secondary demethanizer, 5 the C2 splitter and 6 the compressor. On top of the primary demethanizer there are a condenser, a decanter producing a liquid phase sent as a reflux to said primary demethanizer and a gaseous phase which is the overhead, they are not shown on the FIG. 3. The overhead of the primary demethanizer is sent to the compressor. On the bottom of the primary demethanizer there is a reboiler not shown on FIG. 3. The secondary demethanizer and the C2 splitter have each a similar equipment not shown on FIG. 3.

The contaminated ethylene stream (A) comprising essentially ethylene, up to 1 w % oxygenates, ethane, CO, CO2, H2, CH4 and C3+ hydrocarbons has been dried is sent to a primary demethanizer 1 to produce an overhead stream comprising essentially CO, H2, CH4 and a portion of ethylene and ethane,
a bottom stream comprising essentially ethylene, oxygenates, ethane, CO2 and C3+ hydrocarbons,
the overhead stream of demethanizer 1 is sent through a compressor 6 to a secondary demethanizer 4 to produce
an overhead stream comprising essentially CO, H2 and CH4,
a bottom stream comprising essentially ethylene, oxygenates, ethane, CO2 and C3+ hydrocarbons,
said bottom stream of secondary demethanizer 4 and said bottom stream of primary demethanizer 1 are sent to a C2 splitter 5 to produce
a bottom stream comprising essentially ethane, oxygenates and C3+ hydrocarbons,
an overhead stream consisting essentially of ethylene and CO2,
said overhead of the C2 splitter 5 is sent to a fixed bed CO2 adsorption zone 2-3 to recover an ethylene stream essentially free of CO2.

In a specific example the pressure of the primary demethanizer ranges from 15 to 25 barg, the pressure of the secondary demethanizer ranges from 40 to 50 barg, the pressure of the C2 splitter is essentially at the same pressure as the primary demethanizer except the pressure drop for transfer of fluids and ranges from 15 to 25 barg and the pressure of the CO2 adsorbers is about 1 or 2 barg less corresponding to the pressure drop due to pipes and equipment. In these ranges of pressure the top of the primary demethanizer is in a temperature range of −25 to −35° C., condensed at a temperature ranging from −25 to −35° C., the temperature in the bottom of the primary demethanizer ranges from −30 to −20° C., the top of the secondary demethanizer is in a temperature range of −10 to 0° C., is condensed at a temperature ranging from −30 to −40° C., the temperature in the bottom of the secondary demethanizer ranges from 0 to 10° C., the top of the C2 splitter is in a temperature range from −25 to −35° C., is condensed in a temperature range from −25 to −35° C., and the temperature in the bottom of the C2 splitter ranges from 75 to 85° C.

Preferably the pressure of the primary demethanizer ranges from 18 to 22 barg, the pressure of the secondary demethanizer ranges from 43 to 47 barg, the pressure of the C2 splitter is essentially at the same pressure as the primary demethanizer except the pressure drop for transfer of fluids and ranges from 18 to 22 barg and the pressure of the CO2 adsorbers is about 1 or 2 barg less corresponding to the pressure drop due to pipes and equipment. In these ranges of pressure the top of the primary demethanizer is in a temperature range of −25 to −31° C., condensed at a temperature ranging from −27 to −32° C., the temperature in the bottom of the primary demethanizer ranges from −28 to −22° C., the top of the secondary demethanizer is in a temperature range of −6 to −2° C., condensed at a temperature ranging from −30 to −35° C., the temperature in the bottom of the secondary demethanizer ranges from 3 to 8° C., the top of the C2 splitter is in a temperature range from −28 to −32° C., is condensed in a temperature range from −28 to −32° C., and the temperature in the bottom of the C2 splitter ranges from 78 to 82° C.

EXAMPLES

Figure 4:
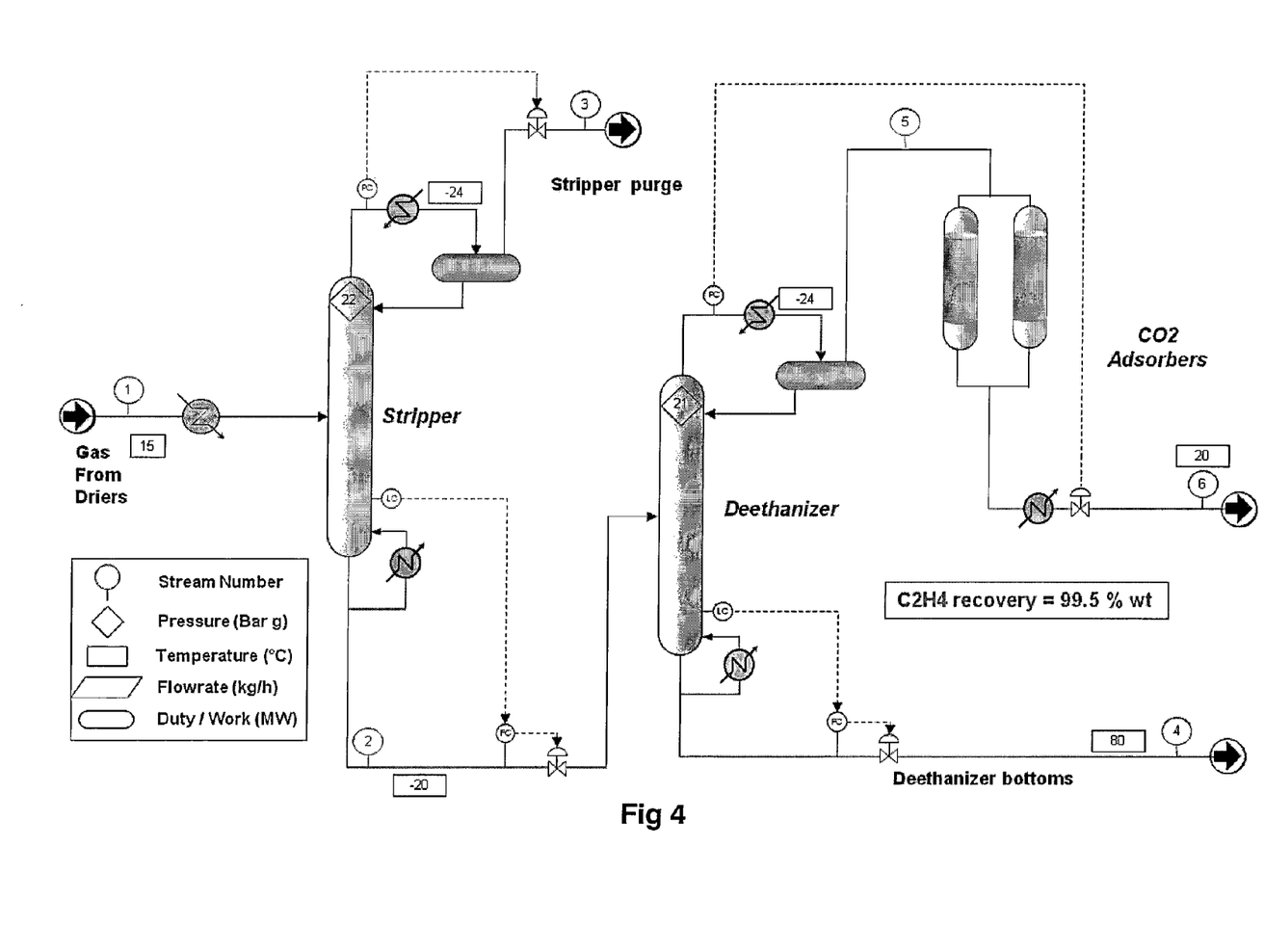
FIG. 4 depicts a process derived from the first embodiment shown in FIG. 1, in which condensers and reboilers are inserted.

The process according to FIG. 4 is operated. FIG. 4 is derived from FIG. 1 by insertion of condensers and reboilers. The results are on the following table.

| | | stream No on fig 4 | | |
|---|---|---|---|---|
| | | 1 Stripper feed | 2 Stripper bottoms | 3 Stripper purge |
| Temperature | ° C. | 15 | −20 | −24 |
| Pressure | bar g | 22 | 22 | 22 |
| H2 | kg/h | 0.1 | | 0.1 |
| CO | kg/h | 1 | | 1 |
| CO2 | kg/h | 1 | 1 | |
| ethane | kg/h | 5 | 5 | |
| ethylene | kg/h | 25091 | 25013 | 78 |
| acetaldehydes | kg/h | 18 | 18 | |
| C3+ | kg/h | 325 | 325 | |
| Total | kg/h | 25441.1 | 25362 | 79.1 |

| | | stream No on fig 4 | | |
|---|---|---|---|---|
| | | 4 Deethanizer bottoms | 5 Deethanizer vapor distillate | 6 Ethylene product |
| Temperature | ° C. | 80 | −24 | 20 |
| Pressure | bar g | 21 | 21 | 20 |
| H2 | kg/h | | | |
| CO | kg/h | | | |
| CO2 | kg/h | | 1 | |
| ethane | kg/h | | 5 | 5 |
| ethylene | kg/h | 18 | 24995 | 24995 |
| acetaldehydes | kg/h | 18 | | |
| C3+ | kg/h | 325 | | |
| Total | kg/h | 361 | 25001 | 25000 |

The invention claimed is:

1. A process for removing oxygenated contaminants from an ethylene stream comprising:
   a) providing a dried ethylene stream (A) comprising essentially ethylene, up to 1 w % oxygenates, ethane, CO, $CO_2$, $H_2$, $CH_4$ and $C_{3+}$ hydrocarbons;
   b) sending the dried ethylene stream (A) to a stripper to produce an overhead stream comprising essentially CO, $H_2$ and $CH_4$; and a bottom stream comprising essentially ethylene, oxygenates, ethane, $CO_2$ and $C_{3+}$ hydrocarbons; and
performing step (i) or step (ii);
wherein step (i) comprises:
   c) sending said bottom stream of step b) to a deethanizer to produce a bottom stream comprising essentially ethane, oxygenates and $C_{3+}$ hydrocarbons; and an overhead stream consisting essentially of ethylene and $CO_2$;
   d) sending the overhead of step c) to a fixed bed $CO_2$ adsorption zone to recover an ethylene stream essentially free of $CO_2$;
wherein step (ii) comprises:
   c1) sending the bottom stream of step b) to a fixed bed $CO_2$ adsorption zone to recover a stream essentially free of $CO_2$, then sending the stream essentially free of $CO_2$ to a deethanizer to produce a bottom stream comprising essentially ethane, oxygenates and $C_{3+}$ hydrocarbons; and an overhead stream consisting essentially of ethylene essentially free of $CO_2$.

2. The process of claim 1, wherein the fixed bed $CO_2$ adsorption zone is located at an inlet of the deethanizer.

3. The process of claim 1, wherein a weight ratio of ethane+CO+$CO_2$+$H_2$+$CH_4$+$C_3$+ hydrocarbons to ethylene in the dried ethylene stream (A) is less than 10/90.

4. The process of claim 3, wherein the weight ratio of ethane+CO+$CO_2$+$H_2$+$CH_4$+$C_3$+ hydrocarbons to ethylene in the dried ethylene stream (A) is above 0.1/99.9.

5. The process of claim 4, wherein the weight ratio of ethane+CO+$CO_2$+$H_2$+$CH_4$+$C_3$+ hydrocarbons to ethylene in the dried ethylene stream (A) is less than 5/95.

6. The process of claim 1, wherein a proportion of oxygenates in the dried ethylene stream (A) is from 50 wppm to 7000 wppm.

7. The process of claim 1, wherein a proportion of oxygenates in the dried ethylene stream (A) is up to 3000 wppm.

8. The process of claim 1, wherein the proportion of oxygenates in the dried ethylene stream (A) is up to 2000 wppm.

9. The process of claim 1, wherein a proportion of $H_2$ in the dried ethylene stream (A) is from 5 to 1000 wppm.

10. The process of claim 1, wherein a proportion of $H_2$ in the dried ethylene stream (A) is up to 800 wppm.

11. The process of claim 1, wherein a proportion of $H_2$ in the dried ethylene stream (A) is up to 500 wppm.

12. The process of claim 1, wherein the dried ethylene stream (A) is originated from the dehydration of ethanol.

* * * * *